United States Patent

Papenfuhs et al.

Patent Number: 5,191,126
Date of Patent: Mar. 2, 1993

[54] PROCESS FOR THE PREPARATION OF DIFLUOROBENZALDEHYDES

[75] Inventors: Theodor Papenfuhs, Frankfurt am Main; Andreas Kanschik-Conradsen, Gernsheim/Rhein, both of Fed. Rep. of Germany

[73] Assignee: Hoechst Aktiengesellschaft, Frankfurt am Main, Fed. Rep. of Germany

[21] Appl. No.: 913,150

[22] Filed: Jul. 14, 1992

[30] Foreign Application Priority Data

Jul. 16, 1991 [DE] Fed. Rep. of Germany ....... 4123461

[51] Int. Cl.$^5$ .................... C07C 45/63; C07C 47/55
[52] U.S. Cl. ................................... 568/437; 568/425; 568/426
[58] Field of Search ............. 568/425, 426, 437

[56] References Cited

U.S. PATENT DOCUMENTS 4,845,304 7/1989 Yoshida et al. ............... 568/433
5,041,683 8/1991 Marhold et al. ............... 568/425

FOREIGN PATENT DOCUMENTS 289942 11/1988 European Pat. Off. .......... 568/426
3637156 5/1988 Fed. Rep. of Germany ...... 568/426

Primary Examiner—Werren B. Lone

[57] ABSTRACT

Process for the preparation, in high yields, of difluorobenzaldehydes of the formula (1)

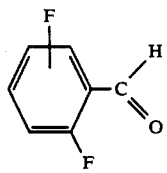

(1)

in which the second fluorine atom is in the 4 or 6 position, by reacting a dichlorobenzaldehyde of the formula (2)

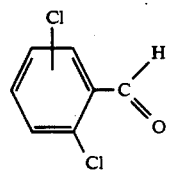

(2)

in which the second chlorine atom is in the 4 or 6 position, with an alkali metal fluoride in a dipolar aprotic solvent in the presence of an ethylene glycol dialkyl ether as catalyst of the formula (3)

$$RO-(CH_2-CH_2-O)_n-R \qquad (3)$$

in which R is a methyl, ethyl or propyl or isopropyl group and n is a number from 1 to about 50, at temperatures of about 160° C. to about 250° C.

8 Claims, No Drawings

PROCESS FOR THE PREPARATION OF DIFLUOROBENZALDEHYDES

The invention relates to an improved process for the preparation of 2,4- and 2,6-difluorobenzaldehyde in high yields by reaction of the corresponding dichlorobenzaldehydes with alkali metal fluorides in a dipolar aprotic solvent in the presence of an ethylene glycol dialkyl ether. Difluorobenzaldehydes are important precursors for the preparation of pharmaceuticals and crop protection agents.

German Patent 3 637 156 discloses that 2,4-dichlorobenzaldehyde can be prepared with potassium fluoride in sulfolane at temperatures of 210°-215° C. in the course of 15 h in a yield of 68% of theory. The weight ratio of 2,4-dichlorobenzaldehyde to sulfolane is said here to be 1:5.7, which produces an unsatisfactory space-time yield.

In addition, European Patent 289 942 discloses the preparation of 4-fluorobenzaldehyde by reaction of 4-chlorobenzaldehyde with potassium fluoride, using tetraphenylphosphonium bromide and tetraethylene glycol dimethyl ether in the absence of a solvent in a yield of 60% of theory. The reaction in the absence of tetraphenylphosphonium bromide does not lead to formation of 4-fluorobenzaldehyde. The disadvantage of this known process lies in the use of the costly tetraphenylphosphonium bromide.

There was therefore considerable interest in a more industrially expedient process for the preparation of the mentioned difluorobenzaldehydes.

It has now, surprisingly, been found that difluorobenzaldehydes of the formula (1)

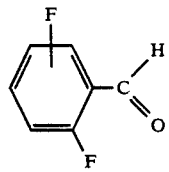

(1)

in which the second fluorine atom is in the 4 or 6 position can be advantageously prepared in high yields by reacting a dichlorobenzaldehyde of the formula (2)

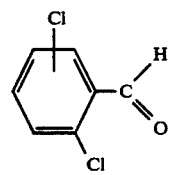

(2)

in which the second chlorine atom is in the 4 or 6 position, with an alkali metal fluoride in a dipolar aprotic solvent in the presence of an ethylene glycol dialkyl ether as catalyst of the formula (3)

RO—(CH$_2$—CH$_2$—O)$_n$—R  (3)

in which R is a methyl, ethyl or propyl or isopropyl group and n is a number from 1 to about 50, at temperatures of about 160° C. to about 250° C., preferably from about 200° C. to about 230° C.

Individual ethylene glycol dialkyl(C$_1$-C$_3$) ethers which may be mentioned as examples are: tetraethylene glycol dimethyl ether, polyethylene glycol dimethyl ether 250, polyethylene glycol dimethyl ether 500, polyethylene glycol dimethyl ether 1000 and polyethylene glycol dimethyl ether 2000. (The numbers given denote the mean molecular weight.)

Alkali metal fluorides which can be used are sodium fluoride, potassium fluoride, rubidium fluoride or cesium fluoride or combinations thereof. Particularly suitable are potassium fluoride, rubidium fluoride or cesium fluoride or combinations thereof.

Suitable dipolar aprotic solvents are for example diphenyl sulfone, tetramethylene sulfone, dimethyl sulfoxide, tetramethylene sulfoxide, dimethylacetamide, dimethylformamide or N-methylpyrrolidone or mixtures thereof.

Starting compounds of the mentioned formula (2) which are used are 2,4- or 2,6-dichlorobenzaldehyde.

As far as the quantitative ratios are concerned, it is expedient to react 1 mol of 2,4- or 2,6-dichlorobenzaldehyde with about 0.8 to about 1.6 mol of alkali metal fluoride, preferably about 1.0 mol to about 1.4 mol.

The ethylene glycol dialkyl ether serving as catalyst is expediently employed in an amount of about 10 to about 50 grams, relative to 1 mol of dichlorobenzaldehyde used.

It is important for carrying out the process that the reaction suspension is thoroughly mixed during the entire reaction.

The process according to the invention is generally carried out at atmospheric pressure. However, overpressure or underpressure can also be employed. Depending on the boiling point of the dipolar aprotic solvent used, employing overpressure may be advantageous.

The examples below serve to illustrate the invention, without limiting it thereto.

EXAMPLE 1

334 g (5.76 mol) of potassium fluoride are suspended in 960 g of sulfolane. 420 g (2.4 mol) of 2,4-dichlorobenzaldehyde and 60 g (0.3 mol) of tetraethylene glycol dimethyl ether are added to the suspension. The mixture is then heated for 13 h at 220° C. under nitrogen with vigorous stirring. All constituents volatile up to 220° C./10 mm Hg are then distilled off from the reaction suspension, as a result of which 312.4 g of a crude distillate are obtained, which, according to gas chromatographic analysis, contains 254.6 g (74.7% of theory) of 2,4-difluorobenzaldehyde and 36.2 g (9.5% of theory) of chlorofluorobenzaldehyde.

By means of subsequent fractionation 245.9 g (72.2% of theory) of 2,4-difluorobenzaldehyde are obtained.

If the reaction is carried out in 1120 g of diphenyl sulfone instead of 960 g of sulfolane and the remainder of the procedure described in Example 1 is followed, virtually the identical result is obtained.

EXAMPLE 2

The process of Example 1 was carried out using 60 g (0.24 mol) of polyethylene glycol dimethyl ether 250 instead of tetraethylene glycol dimethyl ether. In this case, 388.7 g of a crude distillate were obtained which contains, according to gas chromatographic analysis, 252.6 g (74% of theory) of 2,4-difluoronitrobenzene and 33.4 g (8.8% of theory) of chlorofluorobenzaldehyde.

If 1120 g of diphenyl sulfone are employed instead of 960 g of sulfolane and the remainder of the procedure is followed as given, virtually the identical result is obtained.

EXAMPLE 3

The process of Example 1 was carried out using 60 g (0.06 mol) of polyethylene glycol dimethyl ether 1000 instead of tetraethylene glycol dimethyl ether. 314.9 g of a crude distillate were obtained, which contained, according to gas chromatographic analysis, 240.3 g (70.5% of theory) of 2,4-difluorobenzaldehyde and 19.8 g (5.2% of theory) of chlorofluorobenzaldehyde.

We claim:

1. A process for the preparation, in high yield, of a difluorobenzaldehyde of the formula (1)

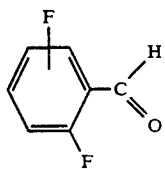
(1)

in which the second fluorine atom is, in the 4 or 6 position, which comprises reacting a dichlorobenzaldehyde of the formula (2)

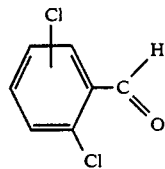
(2)

in which the second chlorine atom is int eh 4 or 6 position, with an alkali metal fluoride in a dipolar aprotic solvent in the presence of an ethylene glycol dialkyl ether as catalyst of the formula (3)

$$RO-(CH_2-CH_2-O)_n-R \quad (3)$$

in which R is a methyl, ethyl or propyl or isopropyl group and n is a number from 1 to about 50, at temperatures of about 160° C. to about 250° C.

2. The process as claimed in claim 1, wherein the reaction is carried out at temperatures of about 200° C. to about 230° C.

3. The process as claimed in claim 1, wherein the reaction is carried out using sodium fluoride, potassium fluoride, rubidium fluoride or cesium fluoride or combinations thereof.

4. The process as claimed in claim 1, wherein the reaction is carried out using potassium fluoride, rubidium fluoride or cesium fluoride or combinations thereof.

5. The process as claimed in claim 1, wherein the dipolar aprotic solvent used is tetramethylene sulfone, dimethyl sulfoxide, tetramethylene sulfoxide, diphenyl sulfone, dimethylacetamide, dimethylformamide or N-methylpyrrolidone or mixtures thereof.

6. The process as claimed in claim 1, wherein the reaction is carried out in the presence of tetramethylene glycol dimethyl ether, polyethylene glycol dimethyl ether 250, polyethylene glycol dimethyl ether 500, polyethylene glycol dimethyl ether 1000 or polyethylene glycol dimethyl ether 2000 as catalyst, the numbers denoting the mean-molecular weight.

7. The process as claimed in claim 1, wherein the reaction suspension is thoroughly mixed during the entire reaction.

8. The process as claimed in claim 1, wherein atmospheric pressure, overpressure or underpressure is employed.

* * * * *